United States Patent

Strumia et al.

[11] 3,938,877
[45] Feb. 17, 1976

[54] HYPERFINE FILTER FOR THE RESONANCE LINES OF CAESIUM AND RUBIDIUM

[75] Inventors: Franco Strumia; Nicola Beverini, both of Pisa, Italy

[73] Assignee: Consiglio Nazionale Della Ricerche, Milan, Italy

[22] Filed: Apr. 10, 1974

[21] Appl. No.: 459,728

[30] Foreign Application Priority Data
Apr. 12, 1973 Italy.................................. 49407/73

[52] U.S. Cl. ................ 350/148; 313/112; 350/157; 356/85
[51] Int. Cl.²........................................... G02B 27/28
[58] Field of Search....... 356/85; 324/.5 AC, .5 AH, 324/.5 F; 350/147, 148, 151, 157; 313/112

[56] References Cited
FOREIGN PATENTS OR APPLICATIONS
918,879  2/1963  United Kingdom.................. 356/85

*Primary Examiner*—Edward S. Bauer

[57] ABSTRACT

A hyperfine filter for the resonance lines of alkali metals, as caesium and rubidium, comprising:

a cell transparent to the light rays and which contains vapours of the alkali metal to be filtered;

means for generating a magnetic field, into which is placed said cell;

a lamp of said metal, means to direct the light beam emitted from the lamp to hit said cell where only one of the two orthogonal components of circular polarization is absorbed;

a circular analyzer provided to separe one of the hyperfine component of the light beam emerging from said cell from the other; and an interference filter to select the particular resonance line which is desired to be used.

8 Claims, 3 Drawing Figures

HYPERFINE FILTER FOR THE RESONANCE LINES OF CAESIUM AND RUBIDIUM

The present invention relates to the hyperfine filters for the resonance lines of alkali metals, and in particular to the hyperfine filters for the resonance lines of caesium and rubidium.

It is well known that the main difficulty in obtaining a hyperfine optical pumping of alkali atoms consists in the filtering of one of the two hyperfine components of the resonance lines. Since the hyperfine structure is less then 0,1 A, the commonly available known kinds of filters are quite useless.

For the $D_1$ line of the caesium a filter has been proposed consisting of an absorption cell placed in a magnetic field orthogonal to the light beam direction, by means of which a good hyperfine optical pumping of the atoms could be obtained only in the lower hyperfine sublevel, but, on the contrary, it was impossible to obtain a sufficient pumping in the upper hyperfine sublevel, as it is necessary for certain applications, as masers. Another type of filter, already known in the art, consists in a glass cylindrical cell containing caesium vapours and placed in a magnetic field parallel to the light beam direction said magnetic field being generated by a cylindric solenoid. Even if the results of this filter may be in part acceptable, it however presents several inconveniences, as, for instance, the difficult of its construction.

As far as the rubidium is concerned, appreciable but not entirely satisfactory results have been achieved by means of a filter using an isotopic dephasing between two stable isotopes.

The filter constructed according to the present invention overcomes several inconveniences of the filters of the prior art and, in any case, it enables to obtain a high efficiency as well as a very good hyperfine filtering of the resonance lines of alkali metals and particularly, of caesium and rubidium.

Thus it is an object of the present invention to provide an improved hyperfine filter for the resonance lines of alkali metals and in particular of caesium or rubidium, which is highly efficient and without the inconveniences present in the analogous types of the filters of the prior art.

The filter, which is the object of the present invention, essentially comprises a cell transparent to the light beam and containing vapours of the alkali metal of which the filtering has to be performed, means for generating a magnetic field into which said cell, is placed a lamp of the metal, of which the filtering has to be performed, the light beam generated from which is caused to hit said cell so that the hyperfine components of the resonance light crossing said cell are absorbed respectively as $\sigma^+$ and $\sigma^-$ radiation by the atoms in the absorption cell, in each hyperfine line only one of the two orthogonal components of circular polarization being absorbed by a circular analyzer separating one of the hyperfine components of the ray coming out of the cell from the other one, and a-n interference filter for selecting the particular resonance line which is desired. The intensity of the magnetic field in which said cell is placed has a value comprised between 3000 and 5000 Gauss and the cell temperature is set up according to the line which will be transmitted and to the useful thickness of said cell in order that said cell contains an optimal amount of vapour of the metal, the filtering of which has to be performed. That may be achieved by introducing the device into a small furnace in order to be able to perform an easier and readier control of the cell temperature and also to attain a more uniform temperature.

The generated magnetic field is parallel to the light beam crossing said cell and circular analyzer; said field can be generated by a device consisting in two horse-shoe permanent magnets positioned according to the well known configuration commonly named "C-magnets."

Other main characteristics of the invention provide that the light beam generated by the lamp of the metal of which the filtering has to be performed is guided by light guides, that the circular analyzer comprises a $\lambda/4$-wave plate and a linear polarizer, and that the circular analyzer can be placed on the opposite position with respect of the lamp, i.e., placing the same just after the lamp and before the light beam generated by this latter hits said cell.

As has hereinabove already stated, the magnetic field has to be higher than 3000 Gauss and lesser than 5000 Gauss.

With reference to the first limit value, it is to be pointed out that this latter depends on the residual coupling between the electronic spin and the electronic spin which is the effect of the sufficiently high intensity of some Zeeman lines which are typical of the magnetic fields of low intensity which must disappear under the Back-Goudsmit effect at higher magnetic fields and which cause the alteration of the absorption process of the components $\sigma^+$ and $\sigma^-$; as far as the second limit is concerned, on account of the fact that at a magnetic field of high intensity the separation between the lines $\sigma$ is greater than that of the hyperfine structure at a zero magnetic field, it is impossible to perform any filtering in these operative conditions.

In order to better understand the invention, a preferred embodiment will be now described which is given merely by way of example and without limiting the invention, reference being made to the accompanying drawings, in which.

Figure 1:
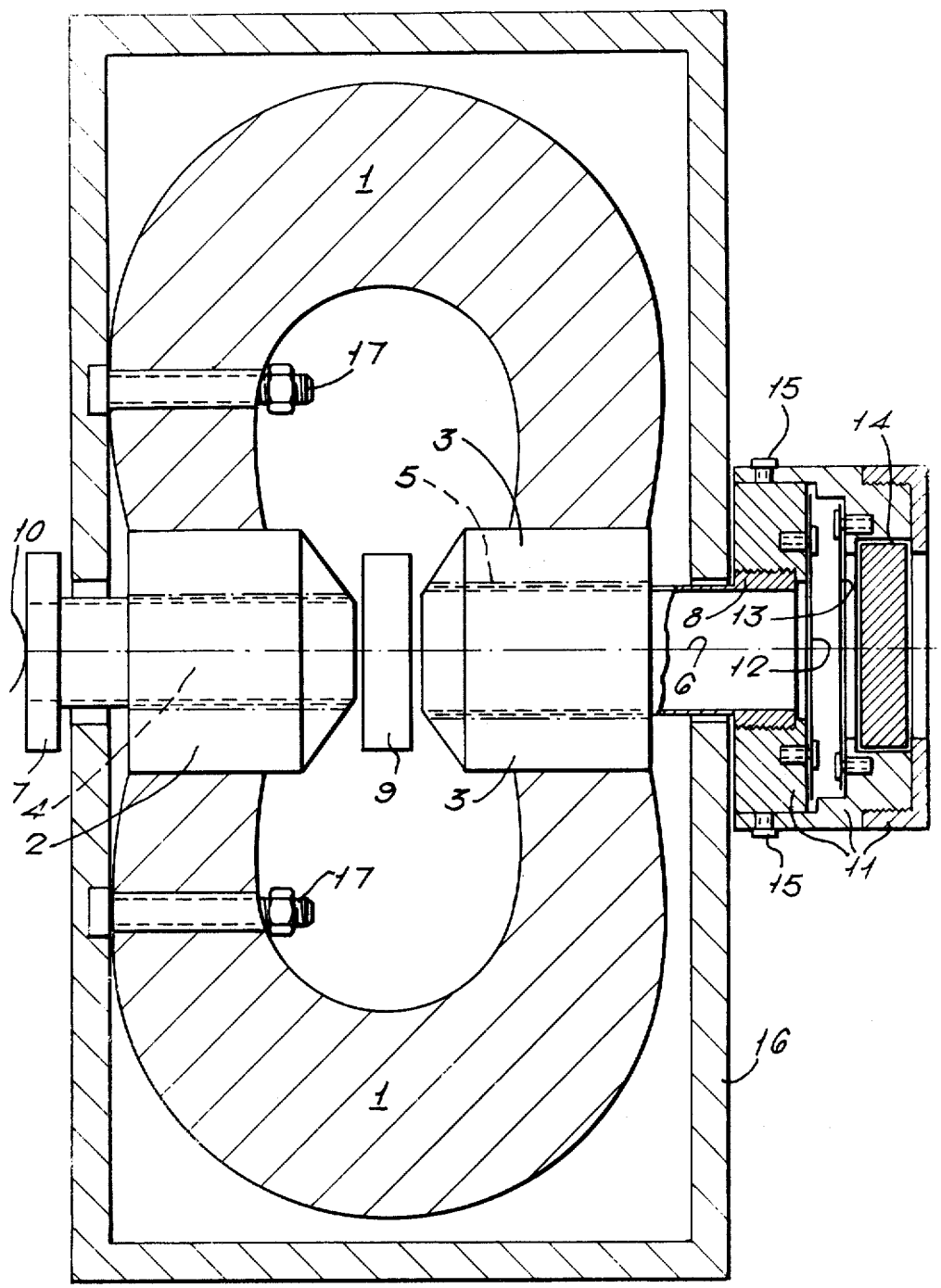
FIG. 1 shows a diagrammatic longitudinal centre sectional view of a filter according to a preferred embodiment of the present invention.

According to this preferred embodiment of the present invention and in order to generate the magnetic fields which are necessary for the operation of the filter two horse-shoe permanent magnets 1 are used arranged in the conventional configuration known under the name "C-magnets," but other suitable magnets could be also used.

The two permanent magnets 1 face two pole shoes 2 and 3 of soft iron provided with through holes 4 and 5 respectively, aligned on the centre axis 6 of the device which is placed in the longitudinal centre plane of the two magnets 1. Two light guides 7 and 8 are provided, each consisting in a copper or brass tube having a polished, silver- or gold-plated inner surface in order to increase its reflecting capacity, said tubes 7 and 8 being introduced into the holes 4 and 5, respectively. At the middle of the two pole shoes 2 and 3 is placed a cell 9 of glass or quarz which is filled with saturated vapour of the metal, the filtering of which has to be performed (in particular, caesium or rubidium). The arrangement is such that a magnetic field is generated about the cell 9 which can vary between 3500 and 5000 Gauss.

In register with the axis 6 and at one side of the device a lamp 10 is located of the metal of which the filtering has to be performed (in particular, caesium or rubidium) so that the light beam generated by the lamp is conveyed by the light guides 7 and 8 so as to become parallel to the magnetic field generated by the two magnets and to cross the cell 9. The light beam coming out of the cell 9 has two hyperfine components of the resonance lines circularly polarized in opposite directions. After said beam having left the light guide 8, it passes through a circular analyzer 11, where one of the hyperfine components is separated from the other.

The circular analyzer usually consists in a $\lambda/4$-wave plate 12 and of a linear polarizer 13 with the addition of an interference filter 14. In the preferred embodiment, the $\lambda/4$-wave plate 12 is constituted of a mica sheet having a suitable thickness and the polarizer is made of Polaroid HN7 manufactured by the Polaroid. The interference filter 14 of any common type serves to select the particular resonance line which is wanted.

By unscrewing the screws 15, the upper part of the analyzer can be rotated through an angle with regard of the $\lambda/4$-wave plate 12, said upper part comprising the polarizer 13 and the interference filter 14. In particular a rotation through an angle of 90° serves to transmit at will either one or the other of the resonance line groups.

In order that the filter can operate, it is necessary that in the cell 9 there is an optimal amount of vapour of the metal, the filtering of which has to be performed (in particular, caesium or rubidium). This is achieved by controlling the cell temperature according to the line which will be wanted and according to the useful thickness of the cell 9, using a small furnace 16 into which is placed the whole filter which is supported and fixed thereto by a set of screw-threaded bolts 17. For instance, in the case as the line $D_2$ of the caesium is concerned and if the cell 9 has a usefull thickness of 5 mm, the optimal temperature is comprised between 95° and 98°C. Using another line or thickness, the temperature must be varied accordingly.

Figure 2:
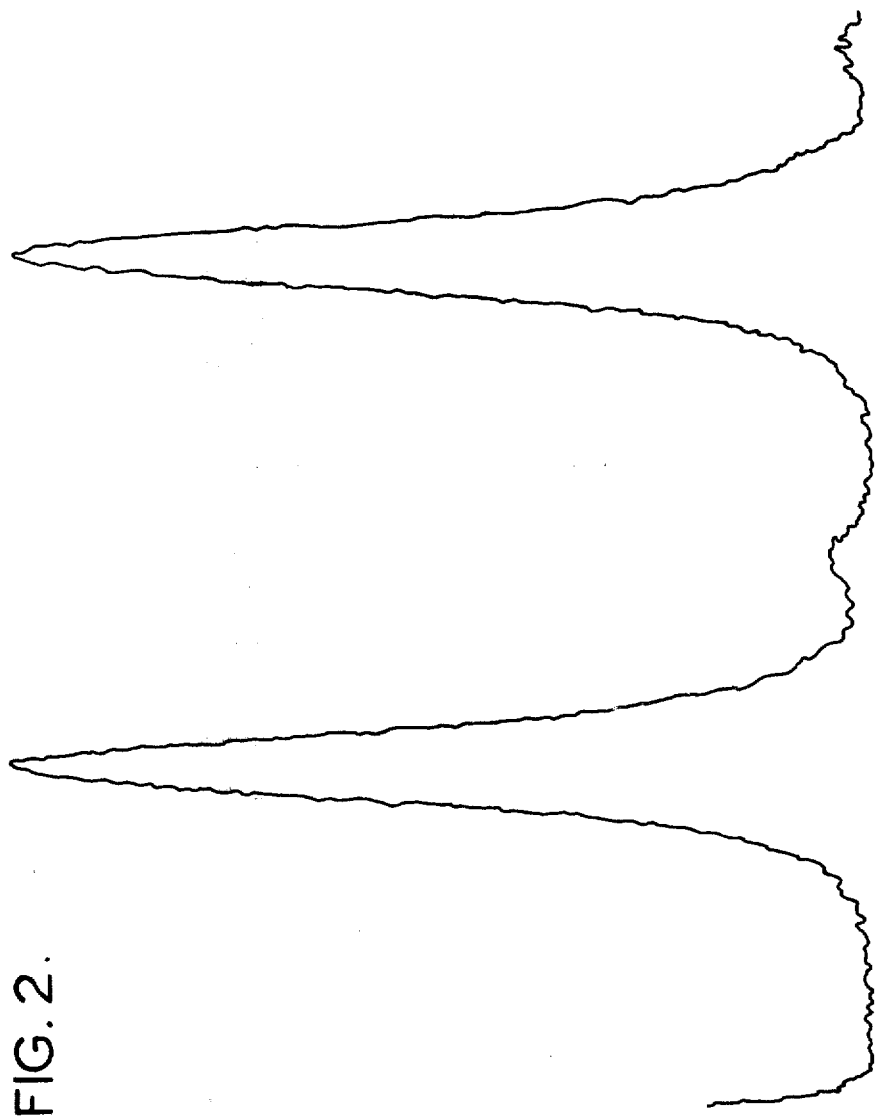
FIG. 2 shows the record of the results of measurements performed with the use of the device shown in FIG. 1 and relating to the line $D_2$ of the caesium and the component F=4.
Figure 3:
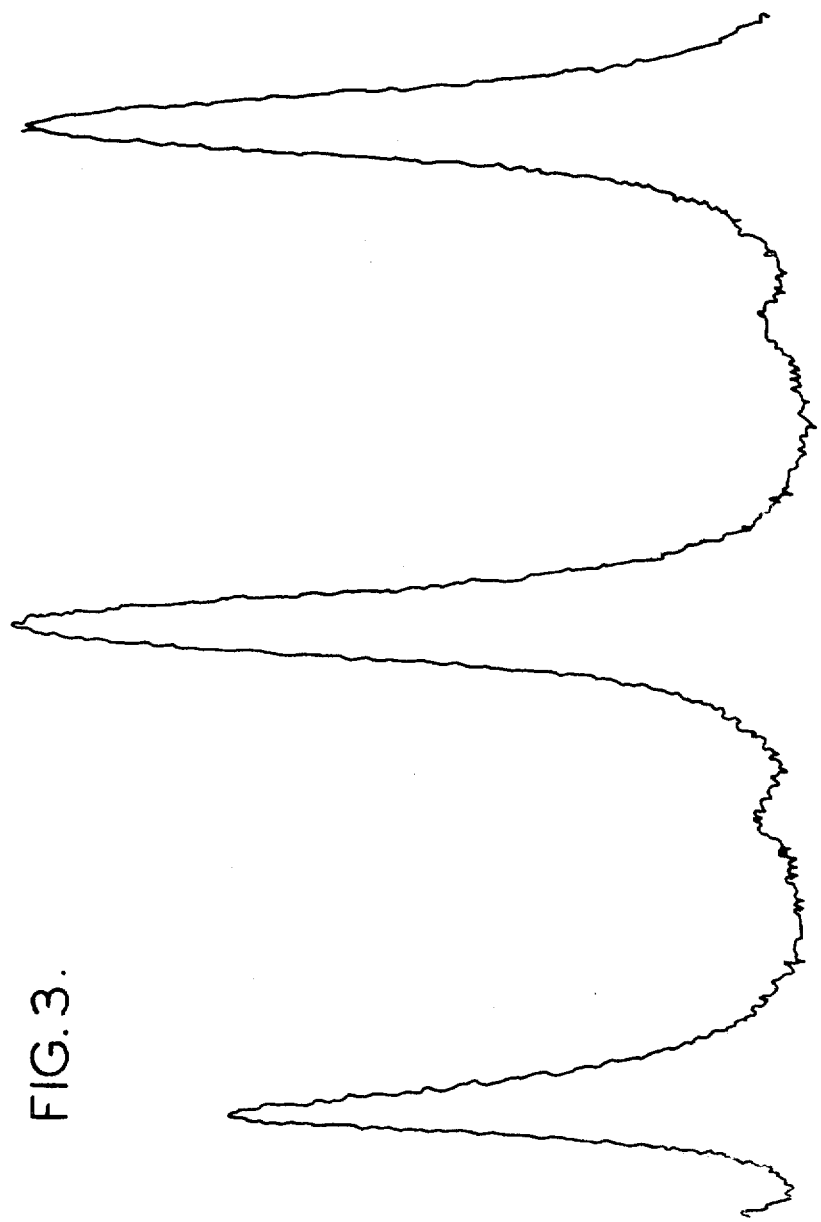
FIG. 3 shows the record of the results of measurements performed with the use of the device shown in FIG. 1 and relating to the line $D_2$ of the caesium and the component F=3.

The filter according to the present invention is very efficient. By way of example in FIGS. 2 and 3 are shown the results of measurements which have been effected in order to control the efficiency of the device of the invention according to one of its preferred embodiments, concerning the line $D_2$ of the caesium. More particularly, in FIG. 2 can be seen the transmission effects of a filter the polarizer 13 of which is so oriented with regard to the $\lambda/4$-wave plate 12 as to transmit the component F=4 and in FIG. 3 can be seen the transmission effects of a filter which has its polarizer oriented with respect of the $\lambda/4$-wave plate 12 so as to transmit the component F=3.

In each of said FIGS. 2 and 3 a linear scale has been used. it will be apparent to the persons skilled in the art, that several modifications can be made in the invention without departing from the field of this invention. For instance, the shown configuration of the "C-magnets" type used for generating the magnetic field could be replaced by "E-magnets" or "thoroidal-magnets" structures.

In addition, it is to be pointed out that the useful thickness of the cell 9 is not at all critical, since it is sufficient to duly modify the operative temperature of the filter to attain an equally high efficiency.

Likewise the position of the circular analyzer in regard to other components can be varied without adversely affecting the device operation. For instance, said analyzer can be positioned just after the lamp, i.e., the filter parts may be mounted according to an opposite disposition with respect to the lamp.

These and other modifications, which will be well evident to the persons skilled in the art, can be made in the device of the invention without departing from its informing principle.

We claim:

1. A hyperfine filter for the resonance lines of the alkali metals, caesium and rubidium which comprises in series, a cell transparent to light rays and which contains vapors of the alkali metal to be filtered;

a device for generating a magnetic field into which said cell is placed;

a lamp of the metal of which filtering is desired, the light beam emitted therefrom being directed to strike said cell so that the two hyperfine components of the resonance line passing through the cell are absorbed by the atoms present in the cell as radiation $6^+$ or $6^-$ respectively so that in each hyperfine line only one of the two orthogonal components of circular polarization is absorbed;

a circular analyzer for separating one of the hyperfine components of the light beam emerging from the said cell from the other and which includes a $\lambda/4$-wave plate and a linear polarizer arranged in series; and an interference filter for selecting the particular resonance line desired.

2. A hyperfine filter according to claim 1, wherein the intensity of the magnetic field adjacent the cell has a value between 3000 and 5000 Gauss.

3. A hyperfine filter according to claim 1, wherein the temperature of the said cell is determined according to the selected line and according to the useful thickness of said cell in order that said cell contains an optimal amount of the vapour of that metal, the filtering of which is to be performed.

4. A hyperfine filter according to claim 1, wherein it is housed within a small furnace to facilitate and temperature control of the said cell and to obtain a more uniform temperature.

5. A hyperfine filter according to claim 1, wherein the generated magnetic field is parallel to the light beam crossing the cell and the circular analyzer.

6. A hyperfine filter according to claim 1, wherein the device for producing the magnetic field comprises two permanent magnets of the horse-shoe structure, having so-called "C-magnets" configuration.

7. A hyperfine filter according to claim 1, wherein the light beam generated by the lamp of the metal of which the filtering is wanted, is conveyed through light guides.

8. A hyperfine filter according to claim 1, wherein the circular analyzer is placed in the opposite position with respect to the lamp, by positioning it just after the lamp and before the light beam generated by said lamp strikes the said cell.

* * * * *